United States Patent [19]
Imanari et al.

[11] Patent Number: 4,757,152
[45] Date of Patent: Jul. 12, 1988

[54] PROCESS FOR PRODUCING INDOLES

[75] Inventors: Makoto Imanari; Hiroshi Iwane; Katsuhumi Kuzira; Takatoshi Seto, all of Ibaraki, Japan

[73] Assignee: Research Association for Utilization of Light Oil, Tokyo, Japan

[21] Appl. No.: 796,739

[22] Filed: Nov. 12, 1985

[30] Foreign Application Priority Data

Nov. 12, 1984 [JP] Japan ................. 59-238030

[51] Int. Cl.⁴ .......................................... C07D 209/08
[52] U.S. Cl. ...................................................... 548/508
[58] Field of Search ........................................ 548/508

[56] References Cited

U.S. PATENT DOCUMENTS 3,699,120 10/1972 Bakke et al. ........................ 548/508
3,984,434 10/1976 O'Murchú ........................... 548/508

FOREIGN PATENT DOCUMENTS 606027 11/1934 Fed. Rep. of Germany .
6005459 1/1981 Japan ................................. 548/508
7619 2/1985 Japan .
2051065 1/1981 United Kingdom ............... 548/508

OTHER PUBLICATIONS

Acta. Chim. Acad. Sci. Hung., 54, 167 (1967).
Derwent Abstract of Japanese Laid-Open Appl. No. 142063, May 19, 1976.
Roczniki, Chem., 38, 507 (1964).
J. Org. Chem., 29, 1540 (1964).
Derwent Abstract of Japanese Patent Publication No. J85007619 (Feb. 1985), Mitsui Petrochem.

*Primary Examiner*—Mary E. Ceperley
*Attorney, Agent, or Firm*—Oblon, Fisher, Spivak, McClelland & Maier

[57] ABSTRACT

A process for producing an indole by catalytic reaction of a 2-(o-aminoaryl)ethanol, said reaction being carried out by heating in a liquid phase in the presence of an alkali metal using a catalyst containing a metal selected from the group consisting of a platinum-group metal, nickel and copper.

The process is industrially advantageous in that indoles are produced in high yield.

8 Claims, No Drawings

PROCESS FOR PRODUCING INDOLES

FIELD OF THE INVENTION

The present invention relates to a process for producing indoles from 2-(o-aminoaryl)ethanols. The present invention provides an industrially advantageous process for producing indoles in high yield. Indoles are useful as starting materials for the industrial production of perfumes, amino acids such as tryptophan, and polymer stabilizers.

BACKGROUND OF THE INVENTION

German Pat. No. 606,027 discloses a process for producing indolines and/or indoles by catalytic gas-phase reaction of 2-(o-aminoaryl)ethanols. A list of the catalysts usable in this process includes Cu, Co, Ni, Ag, Fe, Pd, Pt, Mo, W, Pb, Mn, Al, Ti, Zr, Cr and Th, and $CuCO_3$ is mentioned as a specific example capable of producing indole as the main product. However, none of these catalysts are completely satisfactory for insutrial purposes primarily because their activity is reduced during run.

Methods for producing indoles from indolines by dehydrogenation reaction are also known and they include the use of a Raney nickel catalyst [Acta Chim. Acad. Sci. Hung., 54, 167 (1967)], the use of a chromium or copper-chromium catalyst [Roczniki, Chem., 38, 507 (1964)] and the use of a manganese dioxide catalyst [J. Org. Chem., 29, 1540 (1964)]. However, these catalysts have the disadvantages of low indole yields and selectivities.

Unexamined Published Japanese Patent Application No. 142063/77 discloses a method of producing indoles by heating indolines or 2-(o-aminoaryl)ethanols together with at least one acidic compound selected from the group consisting of nitric acid, nitrous acid, an acidic sulfate salt and an acidic sulfite salt. This method is not industrially feasible, either, since it consumes a large amount of catalyst.

Japanese Patent Publication No. 7619/85 proposes a one-step production process of indole by heating o-(2-nitrophenyl)ethanol in the liquid state in the presence of hydrogen and a reducing catalyst, in order to improve the industrial disadvantage of reduced catalytic activity inevitable in a gas-phase process for producing indole from o-(2-nitrophenyl)ethanol in a single step (Japanese Patent Publication No. 20778/74). According to the Publication, the catalyst used in this process experiences a relatively small activity loss even if a large amount of the starting material is processed. However, a large quantity of catalyst is necessary for the purpose of cyclic use and the yield of indole produced per unit amount of catalyst is low. The present inventors repeated this prior art method and found that it is not industrially feasible because of the very low yield of indole obtained (see Referential Examples 1 to 3 given later in this specification).

SUMMARY OF THE INVENTION

With a view to developing an industrially advantageous process for producing high yields of indoles from readily available and inexpensive materials at low catalyst costs, the present inventors made extensive research covering both starting materials and catalysts. The present invention has been accomplished on the basis of these research efforts.

The present invention therefore provides a process for producing an indole by catalytic reaction of a 2-(o-aminoaryl)ethanol which is heated in a liquid phase in the presence of an alkali metal using a catalyst containing a metal selected from the group consisting of a platinum-group metal, nickel and copper. The process of the present invention is industrially advantageous in that it requires a small catalyst loading and achieves high indole yield at an increased reaction rate.

DETAILED DESCRIPTION OF THE INVENTION

Starting material

The 2-(o-aminoaryl)ethanol used in the process of the present invention is a compound represented by the following formula:

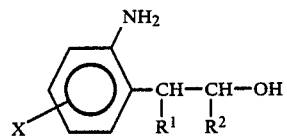

where X is hydrogen, a $C_{1-12}$ alkyl group, a $C_{1-12}$ alkoxy group, a halogen atom or a hydroxyl group; $R^1$ and $R^2$ which may be the same or different each is a substituent selected from the group consisting of hydrogen, a $C_{1-4}$ alkyl group, a $C_{5-6}$ cycloalkyl group and a $C_{6-10}$ aryl group.

Examples of the 2-(o-aminoaryl)ethanols represented by the above formula are as follows: 2-(o-aminophenyl)ethanol, 2-(2-amino-5-isopropylphenyl)ethanol, 2-(2-amino-5-tert-butylphenyl)ethanol, 2-(2-amino-5-fluorophenyl)ethanol, 2-(2-amino-5-hydroxyphenyl)ethanol, 2-(2-amino-3-methoxyphenyl)ethanol, 2-(2-amino-6-methoxyphenyl)ethanol, 1-methyl-2-(o-aminophenyl)ethanol, 1-ethyl-2-(o-aminophenyl)ethanol, 1-isopropyl-2-(o-aminophenyl)ethanol, 1-cyclohexyl-2-(o-aminophenyl)ethanol, 2-(2-amino-6-benzyloxyphenyl)ethanol, 1-phenyl-2-(o-aminophenyl)ethanol, 2-methyl-2-(o-aminophenyl)ethanol, 2-phenyl-2-(o-aminophenyl)ethanol, and 1-phenyl-2-(2-amino-5-methoxyphenyl)ethanol.

Catalyst:

The catalyst used in the process of the present invention contains a metal selected from the group consisting of a platinum-group metal, nickel and copper and is associated with at least one alkali metal such as lithium, sodium, potassium, rubidium or cesium. A catalyst containing a metal selected from the group consisting of a platinum-group metal, nickel and copper associated with either potassium or sodium as an alkali metal is preferred from the viewpoint of indole yield.

The alkali metal may be either incorporated in the catalyst or directly added to the reaction system. The alkali metal is used in an amount ranging from $10^{-4}$ to 10 g, preferably $5 \times 10^{-4}$ to 1 g, per gram of the 2-(o-aminoaryl)ethanol used as the starting material.

Illustrative platinum-group metals are ruthenium, rhodium, palladium, osmium, iridium, and platinum and among these, palladium, platinum and ruthenium are preferred, with palladium being particularly preferred.

The catalyst containing a metal selected from the group consisting of a platinum-group metal and nickel associated with the alkali metal may be used as it is in the indole-producing reaction but, if desired, the catalyst may be supported on a carrier. Illustrative carriers include metal oxides, active carbon, carbon black, graphite, metal sulfate salts, metal carbonate salts, and metal phosphate salts. Specific examples are active carbon, carbon black, alumina, silica, titania, diatomaceous earth, and mixed oxides such as silica-alumina, titania-silica, titania-magnesia, silica-magnesia and alumina-titania. Active carbon is particularly preferred for use with platinum-group metals, while diatomaceous earth is preferred for use with nickel.

Other preferred catalysts are Raney nickel and Raney copper.

The state of the metal and alkali metal present as the active components of the catalyst used in the process of the present invention is not limited to any particular form, no matter whether the catalyst is virgin, in the course of run or no longer used. For example, platinum-group metals may be in the form of elements, metal oxides or metal halides; nickel may be either elemental or in a slightly oxidized (e.g., surface-oxidized) form; copper may be in an elemental form; and alkali metals may be in the form of metal oxides, metal carbonate salts, metal sulfate salts, metal halides or metal phosphate salts.

The catalyst used in the present invention may contain a third component such as various metals and metal compounds that will not appreciably impair the catalytic activity. Examples of this third component include alkaline earth metals, metals of IB group such as copper and silver, metals of VIII group such as iron, cobalt and nickel, metals of VII group such as manganese, metals of VI group such as chromium, molybdenum and tungsten, metals of V group such as vanadium, metals of IV group such as tin and lead, metals of IIB group such as zinc and cadmium, metals of III group such as boron, and the metal compounds thereof.

The catalyst described above are used in an amount of $10^{-4}$ to 10 g, preferably $5 \times 10^{-4}$ to 1 g, per gram of the starting 2-(o-aminoaryl)ethanol in general.

If a platinum-group metal is used as an active component in the catalyst in accordance with the present invention, a reaction system contains $10^{-5}$ to 10 moles, preferably $10^{-4}$ to 1 mole, of the platinum-group metal, and $2 \times 10^{-5}$ to 20 moles, preferably $2 \times 10^{-4}$ to 2 moles, of an alkali metal per mole of the starting 2-(o-aminoaryl)ethanol.

A catalyst having nickel supported on diatomaceous earth in the virgin state contains 30 to 80 wt%, preferably 40 to 70 wt%, of nickel in elemental form.

Nickel and copper catalysts of Raney type may be prepared by activating Al-Ni alloy, and Al-Cu alloy, respectively, with an aqueous solution of sodium hydroxide in accordance with conventional techniques, for example, by the method described in "Shokubai Binran (Catalyst Handbook)", ed. by the Catalysts Society of Japan, Chijin Shokan, pp. 482–486. According to this method, 1 volume of the specific alloy is charged bit by bit into 1.3 to 1.5 volume of a 20 to 25% aqueous solution of sodium hydroxide at 50° to 60° C. while cooling under thorough agitation, with care taken to remove any hydrogen evolved; thereafter, the solution is stirred at 50° to 100° C. for 30 to 120 minutes in order to remove aluminum. If the agitation is inadequate, the catalyst is insufficiently activated to provide the desired activity. The catalyst recovered from the NaOH solution is usually washed by decantation with 8 to 9 times the volume of the alloy of water until the pH of the washings comes to be within the range of 8 to 9.

Reaction conditions:

In accordance with the process of the present invention, the desired indoles may be produced in high yield by simply heating the starting 2-(o-aminoaryl)ethanols in the presence of the catalyst described above and an alkali metal. The temperature at which the reaction system is heated generally ranges from 130° to 300° C., preferably from 150° to 250° C. Above 300° C., side reactions will occur to an undesirable extent. Below 130° C., the reaction rate is slowed down to prolong the reaction period. The reaction time is not limited to any particular range but is generally set between about 0.1 and about 20 hours.

The reaction should be carried out at a pressure sufficient to maintain at least a part of the 2-(o-aminoaryl)ethanol in the liquid phase. Atmospheric pressure is generally used but the reaction may be performed under reduced pressure or under pressure if at least a part of the 2-(o-aminoaryl)ethanol can be maintained in the liquid phase.

It is preferable to stir the reaction solution either by using conventional agitating blades or by blowing nitrogen or other inert gases into the reaction system. Stirring the reaction solution is effective for the purpose of attaining improved selectivity for indoles. The reaction will proceed satisfactorily in the absence of a solvent. The indoles produced may be continuously recovered while water and hydrogen forming as by-products are removed from the reaction system. In this case, the 2-(o-aminoaryl)ethanol is preferably fed into the reactor in a continuous manner. If desired, a solvent may be used in performing the reaction and preferred solvents are those which will boil at higher temperatures than the product indoles.

The following examples, comparative examples and referential examples are provided for the purpose of further illustrating the process of the present invention. The yields of the products obtained in the following examples and comparative examples are indicated in terms of mol% of the 2-(o-aminoaryl)ethanols used as starting materials.

EXAMPLE 1

A Pyrex flask equipped with a single-distillator (distillation head, condenser, adapter and receptacle) and a $N_2$ gas blowing pipe was charged with 2 g (14.6 mmol) of 2-(o-aminophenyl)ethanol and 0.3 g of Pd·K—C catalyst (Pd: 0.13 mmol) prepared by supporting 5 wt% of $K_2CO_3$ on a 5 % Pd—C catalyst available from Nippon Engelhard Ltd. After putting a magnetic stirrer into the flask, the latter was placed over an oil bath heated at 185° to 195° C. Reaction was carried out for 4 hours while nitrogen gas was blown into the flask. After completion of the reaction, the product was recovered with the aid of ethanol. Gas chromatographic analysis of the product showed that the conversion of 2-(o-aminophenyl)ethanol and the yield of indole were 100% and 88.8%, respectively. Very small amounts of by-products were identified by gas chromatography.

EXAMPLE 2

The procedures of Example 1 were repeated except that the amount of the Pd·K—C catalyst was decreased to 0.15 g (Pd: 0.067 mmol). The conversion of 2-(o-aminophenyl)ethanol and the yield of indole were 93.9% and 75.4%, respectively.

EXAMPLE 3

The procedures of Example 1 were repeated except that the amount of $K_2CO_3$ supported on the Pd·K—C catalyst, the amount of the catalyst used and the amount of the 2-(o-aminophenyl)ethanol supplied as the starting material were changed to 10 wt%, 0.1 g (Pd: 0.042 mmol) and 1.36 g (9.93 mmol), respectively. The conversion of 2-(o-aminophenyl)ethanol and the yield of indole were 91.9% and 68.6%, respectively.

EXAMPLE 4

By repeating the procedures of Example 1, a reaction solution exhibiting a 2-(o-aminophenyl)ethanol conversion of 100% and an indole yield of 86.2% was obtained. It was subjected to filtration by suction and the residue retained on the filter was washed with ethanol to recover the catalyst. The procedures of Example 1 was repeated except that the recovered catalyst was used. The conversion of 2-(o-aminophenyl)ethanol and the yield of indole were 100% and 91.6%, respectively. Such cyclic use of the catalyst was repeated three more times, and the results of the 4th run of reaction were as follows: the conversion of 2-(o-aminophenyl)ethanol, 83.9%, and the yield of indole, 54.9%. From the reaction solution, 0.24 g of the catalyst was recovered. The recovered catalyst was regenerated by supporting 12 mg (5wt%) of $K_2CO_3$. The procedures of Example 1 was repeated except that the so regenerated catalyst was used. The conversion of 2-(o-aminophenyl)ethanol was 100% and the yield of indole was 87.7%.

EXAMPLE 5

An apparatus of the same type as used in Example 1 was charged with 2 g of n-eicosane (as solvent), 2 g of 2-(o-aminophenyl)ethanol and 0.3 g of Pd·K—C catalyst supporting 5 wt% of $K_2CO_3$ on 5% Pd—C. The oil bath was heated a 185° to 195° C. and reaction was conducted with $N_2$ being blown for 1 hour. Thereafter, the supply of $N_2$ gas was enhanced to distill off the product indole. The distillate was dissolved in ethanol and subjected to gas chromatographic analysis: the conversion of 2-(o-aminophenyl)ethanol was 100% and the yield of indole was 88.3%.

EXAMPLES 6 TO 9

Reaction was carried out as in Example 1 except that the catalyst was changed to those indicated in Table 1. The results of the reaction are also shown in Table 1.

TABLE 1

| Ex. No. | Catalyst | Amount of Catalyst (g) | OAPE* Conversion (%) | Indole Yield (%) |
|---|---|---|---|---|
| 6 | Pd.Na—C | 0.3 | 100 | 85.5 |
| 7 | Pd.Cs—C | 0.3 | 84.0 | 61.6 |
| 8 | Pt.K—C | 0.3 | 54.3 | 50.2 |
| 9 | Ru.K—C | 0.3 | 79.8 | 74.7 |

*2-(o-aminophenyl)ethanol

COMPARATIVE EXAMPLE 1

A Pyrex flask equipped with a Dimroth condenser was charged with 1.37 g (10 mmol) of 2-(o-aminophenyl)ethanol and 0.95 g (7 mmol) of acidic potassium sulfate. After putting a magnetic stirrer into the flask, reaction was conducted at 220° C. for 1 hour. The reaction mixture was neutralized with an aqueous solution of sodium carbonate and subjected to extraction with ether. Gas chromatographic analysis of the ether layer revealed that an indole was obtained in a yield of 6.2%. The indoline yield was 8.2%.

COMPARATIVE EXAMPLE 2

Reaction was carried out as in Example 1 except that the catalyst used was 0.3 g of 5% Pd—C available from Nippon Engelhard Ltd. The conversion of 2-(o-aminophenyl)ethanol was 77.3% and the yield of indole was 47.5%.

EXAMPLE 10

A reactor of the same type as used in Example 1 was charged with 4.0 g (29.2 mmol) of 2-(o-aminophenyl)ethanol, 0.015 g of "N-103" (the nickel/diatomaceous earth catalyst with 49 of 52% Ni available from Nikki Chemical Co., Ltd.) and 0.06 g (0.4 mmol) of potassium carbonate. After putting a magnetic stirrer into the reactor, reaction was performed for 7 hours on an oil bath (190° to 200° C.) while nitrogen gas was blown into the reactor. The conversion of 2-(o-aminophenyl)ethanol was 100% and the yield of indole was 91.8%. The indoline yield was 5.6%.

EXAMPLE 11

The procedures of Example 10 were repeated except that reaction was carried out for 4 hours using 2 g (14.6 mmol) of 2-(o-aminophenyl)ethanol and 0.45 g of Ni-K/diatomaceous earth as a catalyst. This catalyst was prepared by the following method: 0.7 g of "G-49B" (Ni/diatomaceous earth catalyst with 55% Ni available from Nissan-Girdler Catalyst Co., Ltd.) was added to a solution of 0.035 g of potassium carbonate ($K_2CO_3$) in 4 ml of water, and after leaving the mixture to stand overnight, the water was distilled off under reduced pressure. The so prepare catalyst contained 2.8 wt% of potassium on the basis of "G-49B". The results of the reaction were as follows: the conversion of 2-(o-aminophenyl)ethanol was 100%, and the yield of indole was 87.1%. The indoline yield was 7.0%. As in Example 4, the catalyst was recovered from the reaction solution and used in the second run of reaction. The conversion of 2-(o-aminophenyl)ethanol was 100% and the yield of indole was 88.5%. The indoline yield was 6.4%.

COMPARATIVE EXAMPLE 3

The procedures of Example 10 were repeated using 0.015 g of the catalyst, "N-103", except that reaction was continued for 14 hours on an oil bath heated at 210° C. The conversion of 2-(o-aminophenyl)ethanol was 97.3% and the yield of indole was 96.1%. The indoline yield was 0.6%.

COMPARATIVE EXAMPLES 4 TO 6

The first run of the reaction was carried out as in Example 11 except that the catalyst was changed to those indicated in Table 2. The results of the reaction are also shown in Table 2.

TABLE 2

| Run No. | Catalyst | Amount of Catalyst (g) | OAPE Conversion (%) | Indole Yield (%) | Indoline Yield (%) |
|---|---|---|---|---|---|
| 4 | Ni/Cu/Co-silica (57.3 wt % NiO, 5.6 wt % CuO, 6.4 wt % CoO) | 0.3 | 36.9 | 17.6 | 15.8 |
| 5 | Ni—Al | 0.3 | 12.3 | 2.2 | 2.5 |

TABLE 2-continued

| Run No. | Catalyst | Amount of Catalyst (g) | OAPE Conversion (%) | Indole Yield (%) | Indoline Yield (%) |
| --- | --- | --- | --- | --- | --- |
| | (50.9 wt % NiO with the balance of Al$_2$O$_3$) | | | | |
| 6 | Cu—Al (12.5 to 15 wt % CuO with the balance of Al$_2$O$_3$) | 0.3 | 43.5 | 4.4 | 36.6 |

EXAMPLE 12

A Pyrex flask equipped with a single-distillator (Claisen type connected pipe, condenser, adapter and receptacle) and a N$_2$ gas blowing pipe was charged with 5 g (36.5 mmol) of 2-(o-aminophenyl)ethanol, 0.1 g of "NDT-90" (Raney nickel catalyst of Kawaken Fine Chemical Co., Ltd.) and 0.075 g of potassium carbonate (K$_2$CO$_3$). After putting a magnetic stirrer into the flask, the latter was placed over an oil bath heated at 195° to 200° C. Reaction was carried out for 5 hours with nitrogen gas being blown into the flask.

After completion of the reaction, gas chromatographic analysis of the product showed that the conversion of 2-(o-aminophenyl)ethanol and the yield of indole were 93.0% and 86.0%, respectively. More 5 g of 2-(o-aminophenyl)ethanol was added to the reaction solution and another run of indole production was carried out in succession: the overall conversion of 2-(o-aminophenyl)ethanol was 86.7% and the yield of indole was 80.5%.

EXAMPLE 13

The first run procedures of Example 12 were repeated except that 2 g (14.6 mmol) of 2-(o-aminophenyl)ethanol, 0.1 g of "CDT-60" (Raney copper catalyst of Kawaken Fine Chemical Co., Ltd.) and 0.03 g of potassium carbonate (K$_2$CO$_3$) were used. The conversion of 2-(o-aminophenyl)ethanol and the yield of indole were 98.8% and 93.6%, respectively.

COMPARATIVE EXAMPLE 7

The first run procedures of Example 12 were repeated except that 0.15 g of "NDT-90" was used without K$_2$CO$_3$ and reaction was continued for 9 hours. The conversion of 2-(o-aminophenyl)ethanol was 12.5% and the yield of indole was 10.8%.

COMPARATIVE EXAMPLE 8

The procedures of Example 13 were repeated except that 0.1 g of "CDT-60" was used without K$_2$CO$_3$. The conversion of 2-(o-aminophenyl)ethanol was 28.6% and the yield of indole was 24.3%.

REFERENTIAL EXAMPLE 1

A 120-ml autoclave was charged with 4.45 g (26.6 mmol) of 2-(o-nitrophenyl)ethanol, 15 ml of dioxane and 0.54 g of 5% Ru—C catalyst of Nippon Engelhard Ltd. After purging the atmosphere in the autoclave with hydrogen, the pressure in the autoclave was increased to 20 kg/cm$^2$ and reaction was conducted at 200° C. for 1 hour with agitation. Gas chromatographic analysis of the product revealed that although the conversion of 2-(o-nitrophenyl)ethanol was 100%, the yield of indole on the basis of 2-(o-nitrophenyl)ethanol was only 13.8%.

REFERENTIAL EXAMPLE 2

The procedures of Referential Example 1 were repeated except that the catalyst and the reaction time were changed to 0.59 g of 5% Pd—C of Nippon Engelhard Ltd. and 1.5 hours. The conversion of 2-(o-nitrophenyl)ethanol was 100% and the yield of indole was 39.2%.

REFERENTIAL EXAMPLE 3

A 120-ml autoclave was charged with 4.53 g (27.1 mmol) of 2-(o-nitrophenyl)ethanol, 15 ml of dioxane and 0.45 g (as metal) of "NDT-90" (Raney nickel catalyst of Kawaken Fine Chemicals Co., Ltd.). After purging the atmosphere in the autoclave with hydrogen, the pressure in the autoclave was increased to 30 kg/cm$^2$ and reaction was conducted at 200° C. for 1 hour with agitation. The results were as follows: 100% conversion of 2-(o-nitrophenyl)ethanol, with an indole yield of 1.1%.

While the invention has been described in detail and with reference to specific embodiments thereof, it will be apparent to one skilled in the art that various changes and modifications can be made therein without departing from the spirit and scope thereof.

What is claimed is:

1. A process for producing an indole by catalytic reaction of a 2-(o-aminoaryl)ethanol, which comprises heating said 2-(o-aminoaryl)ethanol in a liquid phase in the presence of a catalyst containing a metal selected from the group consisting of a platinum-group metal, a platinum-group metal oxide, a platinum-group metal halide, nickel, surface-oxidized nickel and copper, in association with an alkali metal oxide, alkali metal carbonate, alkali metal sulfate, alkali metal halide or alkali metal phosphate; and wherein said 2-(o-aminoaryl)ethanol is selected from the group of compounds having the formula:

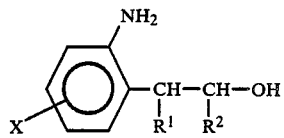

wherein X is hydrogen, a C$_1$-C$_{12}$-alkyl group, a C$_1$-C$_{12}$-alkoxy group, a halogen atom or a hydroxyl group; R$^1$ and R$^2$, which are the same or different, is each a substituent selected from the group consisting of hydrogen, a C$_1$-C$_4$-alkyl group, a C$_5$-C$_6$-cycloalkyl group and a C$_6$-C$_{10}$-aryl group, wherein when said catalyst contains a metal selected from the group consisting of nickel, surface-oxidized nickel and copper said catalyst metal and said alkali metal compound are each used in an amount of about 5×10$^{-4}$ to 1 gram per gram of said 2-(o-aminoaryl)ethanol, and wherein when said catalyst contains a metal selected from the group consisting of a platinum-group metal, a platinum-group metal oxide and a platinum-group metal halide said catalyst metal is used in an amount of about 10$^{-4}$ to 1 mole and said alkali metal compound is used in an amount of about 2×10$^{-4}$ to 2 moles, each per mole of said 2-(o-aminoaryl)ethanol.

2. The process according to claim 1 wherein the catalyst contains a platinum-group metal selected from the group consisting of palladium, platinum or ruthenium.

3. The process according to claim 1 wherein the nickel-containing catalyst contains both nickel and diatomaceous earth.

4. The process according to claim 1 wherein the catalyst containing nickel or copper is selected from the group consisting of Raney nickel and Raney copper.

5. The process according to claim 1 wherein said alkali metal is sodium or potassium.

6. A process according to claim 1 wherein the reaction temperature is within the range of 130° to 300° C.

7. The process according to claim 1, wherein said 2-(o-aminoaryl)ethanol is selected from the group consisting of 2-(o-aminophenyl)-ethanol, 2-(2-amino-5-isopropylphenyl)ethanol, 2-(2-amino-5-tert-butylphenyl)ethanol, 2-(2-amino-5-fluorophenyl)ethanol, 2-(2-amino-5-hydroxyphenyl)ethanol, 2-(2-amino-3-methoxyphenyl)ethanol, 2-(2-amino-6-methoxyphenyl)ethanol, 1-methyl-2-(o-aminophenyl)ethanol, 1-ethyl-2-(o-aminophenyl)ethanol, 1-isopropyl-2-(o-aminophenyl)ethanol, 1-cyclohexyl-2-(o-aminophenyl)ethanol, 2-(2-amino-6-benzyloxyphenyl)ethanol, 2-(2-amino-5-benzyloxyphenyl)ethanol, 1-phenyl-2-(o-aminophenyl)ethanol, 2-methyl-2-(o-aminophenyl)ethanol, 2-phenyl-2-(o-aminophenyl)ethanol, and 1-phenyl-2-(2-amino-5-methoxyphenyl)ethanol.

8. The process according to claim 1, wherein said catalyst is further supported on a carrier selected from the group consisting of metal oxides, active carbon, carbon black, graphite, metal sulfates, metal carbonates and metal phosphates.

* * * * *